United States Patent [19]

Biekart et al.

[11] Patent Number: 5,026,019

[45] Date of Patent: Jun. 25, 1991

[54] ONE-PIECE SLIDABLE HOSE CLAMP

[75] Inventors: Frank T. Biekart; Hubertus E. Hilbrink, both of Emmen, Netherlands

[73] Assignee: NPBI Nederlands Produktielaboratorium voor Bloedtransfusieapparatuur en Infusievloeistoffen B.V., HM Emmer-Compascuu, Netherlands

[21] Appl. No.: 453,953

[22] Filed: Jun. 26, 1990

[30] Foreign Application Priority Data

Jun. 30, 1989 [DE] Fed. Rep. of Germany ....... 3921585

[51] Int. Cl.⁵ .............................................. F16K 7/04
[52] U.S. Cl. ............................................ 251/4; 251/7
[58] Field of Search ........................................ 251/4, 7

[56] References Cited

U.S. PATENT DOCUMENTS

| 2,889,848 | 6/1959 | Redmer | 251/7 X |
| 2,902,248 | 9/1959 | Barton et al. | 251/4 X |
| 2,928,391 | 3/1960 | Krug | 251/4 X |
| 3,103,335 | 9/1963 | Martinez | 251/4 |
| 4,051,578 | 10/1977 | Manschot et al. | 251/4 |

Primary Examiner—John C. Fox
Attorney, Agent, or Firm—Herbert Dubno

[57] ABSTRACT

A clamp for blocking flow through a flexible hose is formed of a one-piece L-shaped body of rigid material having a short leg formed with a generally circular throughgoing hole through which the hose can pass loosely enough for flow through the tube and a long leg formed with a throughgoing slot narrow enough that when the tube passes through it flow through the tube is blocked. The hole and slot communicate with and open into each other at a corner where the two legs join. The clamp is formed with a generally cylindrical passage forming the circular hole. This passage extends along an axis generally parallel to the long leg of the clamp. The cylindrical passage is formed by a pair of like part-cylindrical surfaces having a common centerline and each in turn formed on a wing-like side part of the clamp.

6 Claims, 3 Drawing Sheets

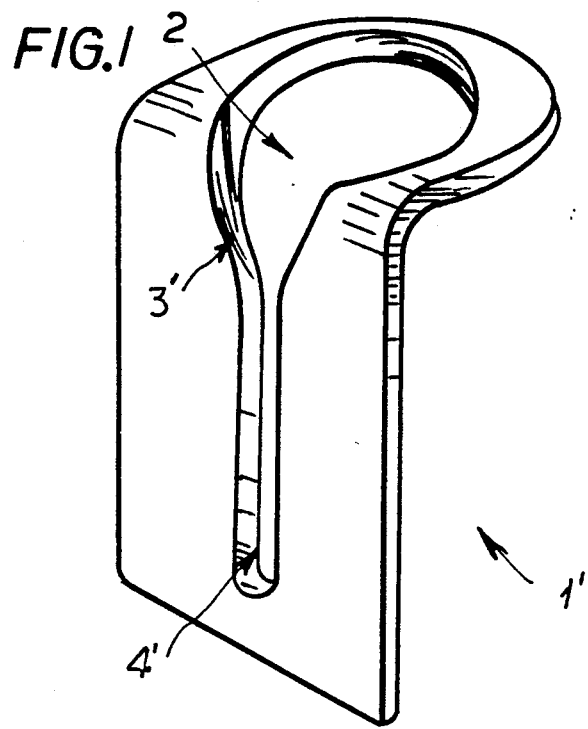
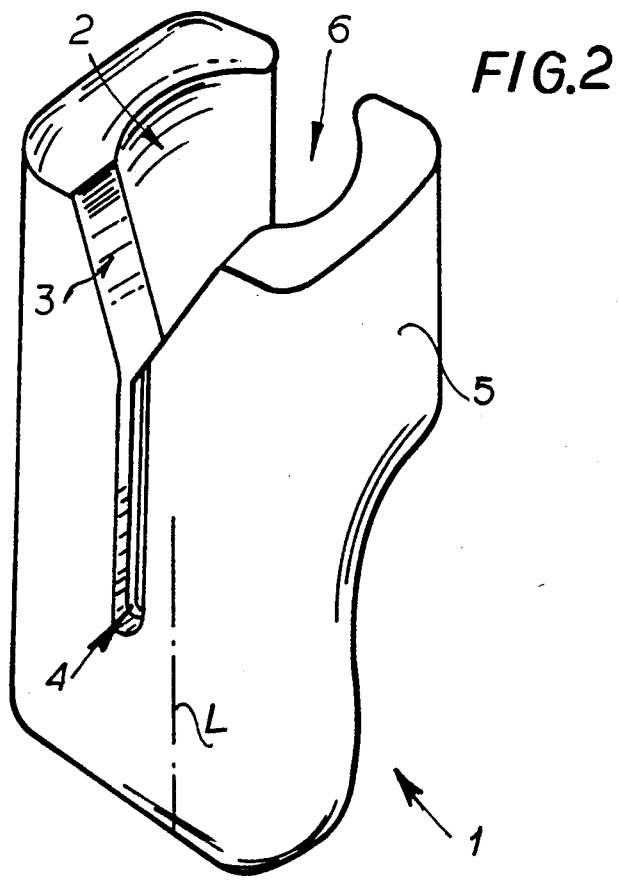

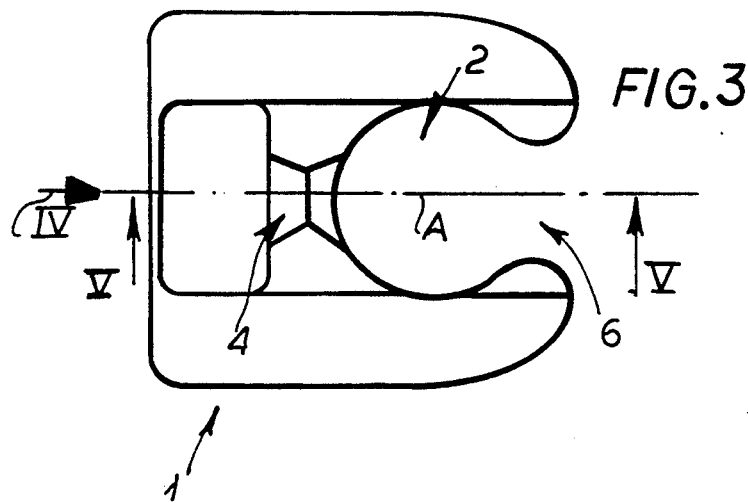
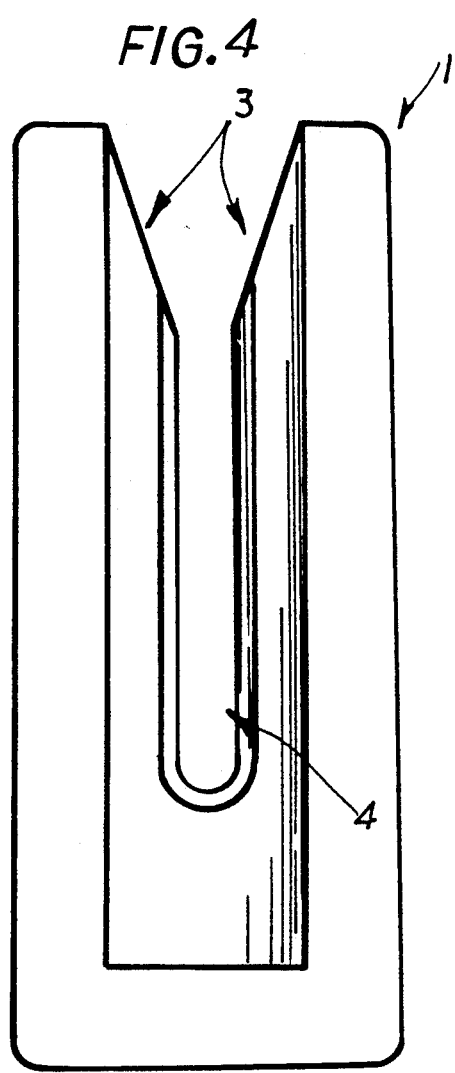
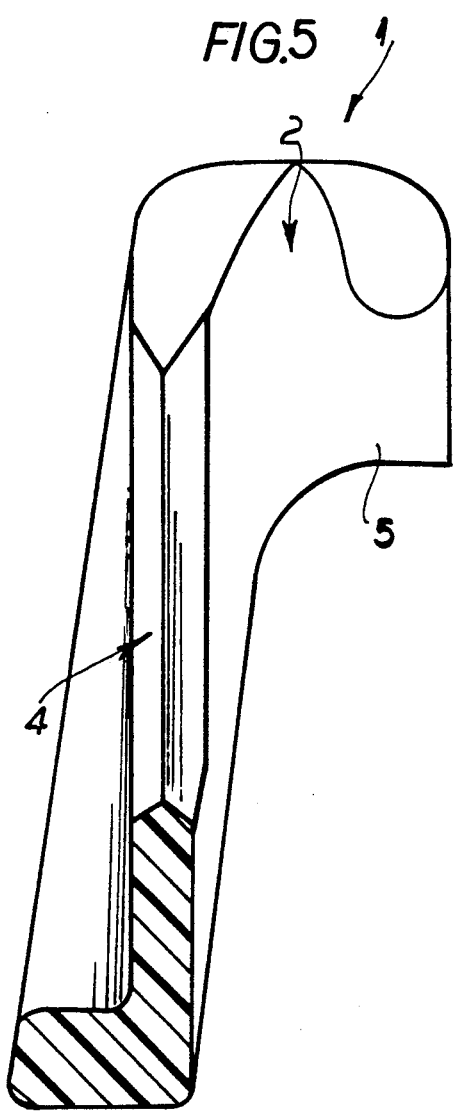

ONE-PIECE SLIDABLE HOSE CLAMP

FIELD OF THE INVENTION

The present invention relates to a hose clamp. More particularly this invention concerns a one-piece clamp usable to block flow along a flexible tube.

BACKGROUND OF THE INVENTION

It is standard to package blood, saline solution, and even some liquid foodstuffs in a bag or pouch whose outlet is formed by a tube that is provided with a clamp. For use the end is cut off the tube and the clamp is then used to block or unblock flow from the tube. Since the container itself is disposable, the clamp must be made as cheaply as possible.

The standard solution is simply to stamp a keyhole-shaped hole in a flat strip of a rigid material. When the tube is positioned in the wide circular end of this hole flow through the tube is possible, and when it is pinched in the slot end of the hole such flow is blocked.

The main problem with such a clamp is that it represents a considerable hindrance. When in the blocking or tube-closed position it extends crosswise of the tube and makes handling and packaging the assembly fairly difficult. In fact it is not uncommon for this transversely projecting rigid item to poke into the pouch and pierce it, thereby destroying the product.

OBJECTS OF THE INVENTION

It is therefore an object of the present invention to provide an improved clamp for a flexible tube.

Another object is the provision of such an improved clamp for a flexible tube which overcomes the above-given disadvantages, that is which does not constitute a substantial hindrance when in the blocking or unblocking position.

SUMMARY OF THE INVENTION

A clamp for blocking flow through a flexible hose according to this invention is formed of a one-piece L-shaped body of rigid material having one leg formed with a generally circular throughgoing hole through which the hose can pass loosely enough for flow through the tube and another leg formed with a throughgoing slot narrow enough that when the tube passes through it flow through the tube is blocked. The hole and slot communicate with and open into each other at a corner where the two legs join.

The clamp according to this invention can be about 60% as long as the standard flat prior-art clamp. When in the open or unblocked position the normally long leg formed with the slot extends parallel to the tube so that it poses virtually no hindrance to packing the container to which the tube is attached.

According to a feature of this invention the clamp is formed with a generally cylindrical passage forming the circular hole. This passage extends along an axis generally parallel to the long leg of the clamp. The cylindrical passage is formed by a pair of like part-cylindrical surfaces having a common centerline and each in turn formed on a wing-like side part of the clamp. This structure allows the clamp to be used as a tube opener, as it can be slid along the tube with the tube in the passage to restore a circular cross-sectional shape to the tube, thereby unflattening it and making it ready for use.

In accordance with further invention features the clamp is formed with a laterally open gap at the circular hole so that the tube can be fitted laterally into the hole through the gap into the hole. This gap is formed opposite the slot so that does not significantly weaken the clamp, while making it possible to reuse it or transfer it to another tube, if necessary.

The clamp according to this invention is injection molded and has a mold-separation line offset from the slot. Thus any structural weakening caused by this line is not at the location of maximum stress, and any flashing or the like from demolding will not directly contact the tube engaged in it. Demolding frequently leaves at the mold-separation line a barb or projection that is quite sharp, so that according to this invention such formation will not damage the tube.

DESCRIPTION OF THE DRAWING

The above and other objects, features, and advantages will become more readily apparent from the following, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing:

FIG. 1 is a perspective view of a first embodiment of the clamp according to this invention;

FIG. 2 is a perspective view of a second embodiment of the clamp of this invention;

FIG. 3 is a top view of the second embodiment;

FIG. 4 is a view taken in the direction of arrow IV of FIG. 3;

FIG. 5 is a section taken along section line V—V of FIG. 3; and

SPECIFIC DESCRIPTION

Figure 6:
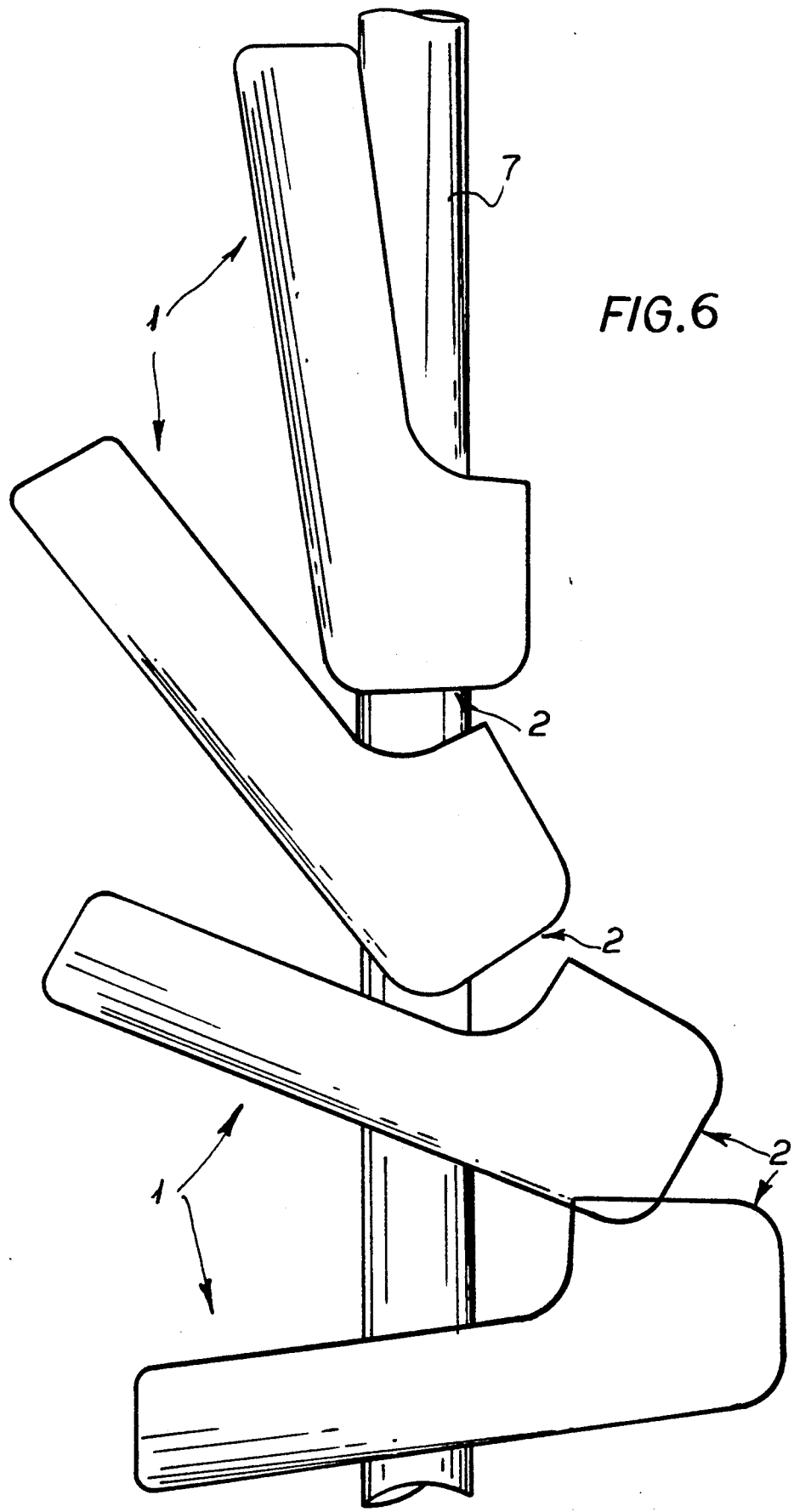
FIG. 6 is a side view illustrating use of the clamp of FIGS. 2 through 5.

As seen in FIG. 1 a clamp 1' is formed of a L-shaped piece of a rigid synthetic resin having a short leg in which is punched a circular hole 2' and a long leg in which is formed an elongated slot 4'. The hole 2' and slot 4' meet and communicate at 3' at the corner where the two legs of the clamp 1 meet.

FIGS. 2 through 5 show a somewhat more massive clamp 1 molded of a block of a durable synthetic resin. It has a short leg formed with a circular hole 2 in fact formed by ends of walls 5 forming a cylindrical passage that also opens laterally at 6. The long leg is formed with a slot 4 that has sharp edges and that flares at 3 where it joins the hole 2. The two sides of the clamp 1 are joined at the end of the slot 4 opposite the hole 2 and the slot 6 is formed at the opposite end, so that the clamp 1 is strongest in the region of the slot where maximum strength is needed. This clamp 1 is made by injection molding and has a mold-separation line L offset completely from the slot 4.

FIG. 6 illustrates how the clamp 1 is fitted around a flexible tube 7 which can extend from a flexible or rigid container filled with liquid. When the tube 7 is engaged in the hole 2 in line with an axis A of this hole 2 the long leg of the clamp 1 lies out of the way against the side of this tube 7 and flow through the tube 7 is possible. Tipping the clamp 1 from this position as illustrated lower down in FIG. 6 slides the tube 7 past the transition region 3 into the slot 4 and pinches it shut therein. Even in the fully blocked position shown at the very bottom of FIG. 6 the clamp has an overall length substantially shorter than the standard prior-art one-piece hose clamp.

We claim:

1. A clamp for blocking flow through a flexible hose, the clamp being formed of a one-piece L-shaped body of rigid material having one leg formed with a generally circular throughgoing hole through which the hose can pass loosely enough for flow through the tube and another leg formed with a throughgoing slot narrow enough that when the tube passes through it flow through the tube is blocked, the hole and slot communicating with and opening into each other.

2. The hose clamp defined in claim 1 wherein the one leg formed with the circular hole is substantially shorter than the other leg.

3. The hose clamp defined in claim 2 wherein the clamp is formed with a generally cylindrical passage forming the circular hole.

4. The hose clamp defined in claim 3 wherein the clamp is formed with a laterally open gap at the circular hole, whereby the tube can be fitted laterally into the hole through the gap into the hole.

5. The hose clamp defined in claim 1 wherein the clamp is injection molded and has a mold-separation line offset from the slot.

6. A clamp for blocking flow through a flexible hose, the clamp being formed of a one-piece L-shaped body of rigid material having
- a short leg formed with a generally circular throughgoing hole through which the hose can pass loosely enough for flow through the tube and
- a long leg formed with a throughgoing slot narrow enough that when the tube passes through it flow through the tube is blocked, the hole and slot communicating with and opening into each other at a corner where the short leg joins the long leg.

* * * * *